US00PP21973P3

(12) United States Plant Patent
Pait et al.

(10) Patent No.: US PP21,973 P3
(45) Date of Patent: Jun. 14, 2011

(54) LOBLOLLY PINE TREE NAMED 'CF LP1-7696'

(50) Latin Name: *Pinus taeda*
Varietal Denomination: CF LP1-7696

(75) Inventors: John Pait, Atlanta, GA (US); Nicholas Muir, Lufkin, TX (US); Stephen Attree, Victoria (CA); Plamen Denchev, Victoria (CA); Robert Weir, Cary, NC (US); Andy Benowicz, Victoria (CA)

(73) Assignee: Cellfor Inc., Saanichton, British Columbia (CA)

( * ) Notice: Subject to any disclaimer, the term of this patent is extended or adjusted under 35 U.S.C. 154(b) by 24 days.

(21) Appl. No.: 12/456,839

(22) Filed: Jun. 23, 2009

(65) Prior Publication Data

US 2010/0325765 P1 Dec. 23, 2010

(51) Int. Cl.
*A01H 5/00* (2006.01)

(52) U.S. Cl. ..... Plt./213

(58) Field of Classification Search ..... Plt./213
See application file for complete search history.

(56) References Cited

U.S. PATENT DOCUMENTS

PP19,447 P3 11/2008 Pait et al.
PP19,793 P3 3/2009 Pait et al.
2007/0079408 P1 4/2007 Pait et al.

OTHER PUBLICATIONS http://web.archive.org/web/20051130221944/http://www.chesapeakebay.net/info/loblolly.cfm (Internet archived Nov. 30, 2005).

http://www.cnr.vt.edu/DENDRO/dendrology/syllabus/factsheet.cfm (1 page), Virginia Tech Department of Forestry, College of National Resources (2007).

United States Patent Office Action for U.S. Appl. No. 11/635,199 dated Dec. 12, 2007.

United States Patent Office Action for U.S. Appl. No. 11/635,703 dated Jan. 18, 2008.

*Primary Examiner* — Annette H Para

(74) *Attorney, Agent, or Firm* — Michael Best & Friedrich LLP

(57) ABSTRACT

A new and distinctive variety of a loblolly pine tree which has been denominated varietally as 'CF LP1-7696' which is distinguished by high growth rate, good resistance to fusiform rust, excellent stem straightness, medium crown width, medium number of whorls, medium branch angle and medium branch diameter.

2 Drawing Sheets

Latin name: *Pinus taeda.*
Variety denomination: 'CF LP1-7696'.

BACKGROUND

A new variety of loblolly pine tree (*Pinus taeda*), has been discovered. This selection has been designated as 'CF LP1-7696.'

This new variety is a progeny of two second generation selections. The female parent is a progeny of two first generation selections made in Cherokee County, Tex. and Tyler County, Tex. The male parent is a progeny of an open pollinated first generation selection made in Montgomery County, Tex.

Cross pollination occurred in early 2000 followed by induction and cryopreservation of embryogenic tissue in 2001. First somatic seedlings were produced in 2002 and planted in early 2003 in three field experiments. A total of 30 ramets were planted at 10 ramets per field experiment. The field experiments are located in Texas and Louisiana.

BRIEF SUMMARY

A new and distinct cultivar of loblolly pine (*Pinus taeda*) is distinctly characterized by high growth rate, good resistance to fusiform rust, excellent stem straightness, medium crown width, medium number of whorls, medium branch angle, medium branch diameter and which is mature for commercial harvesting sooner than conventionally grown trees under the ecological conditions prevailing in the Gulf Coastal Plains of the United States.

The *Pinus taeda* plants of this variety were asexually propagated using an advanced form of micropropagation called somatic embryogenesis carried out at a production facility in Victoria, Canada. Somatic embryogenesis uses a complex process which relies on the splitting of one embryo into many identical embryos. Somatic embryos can then be grown into plants which are all identical genetically. The asexual propagation occurs at an earlier stage in the plant's life cycle than most other micropropagated plants. The detailed methods for somatic embryogenesis used for asexually propagating conifers in general are described in U.S. Pat. No. 6,372,496 and for loblolly pine in particular in U.S. patent application Publication No. 2004/0203150.

BRIEF DESCRIPTION OF THE DRAWINGS

The drawings are color photographs showing the new variety of loblolly pine.

DETAILED BOTANICAL DESCRIPTION

Figure 1:
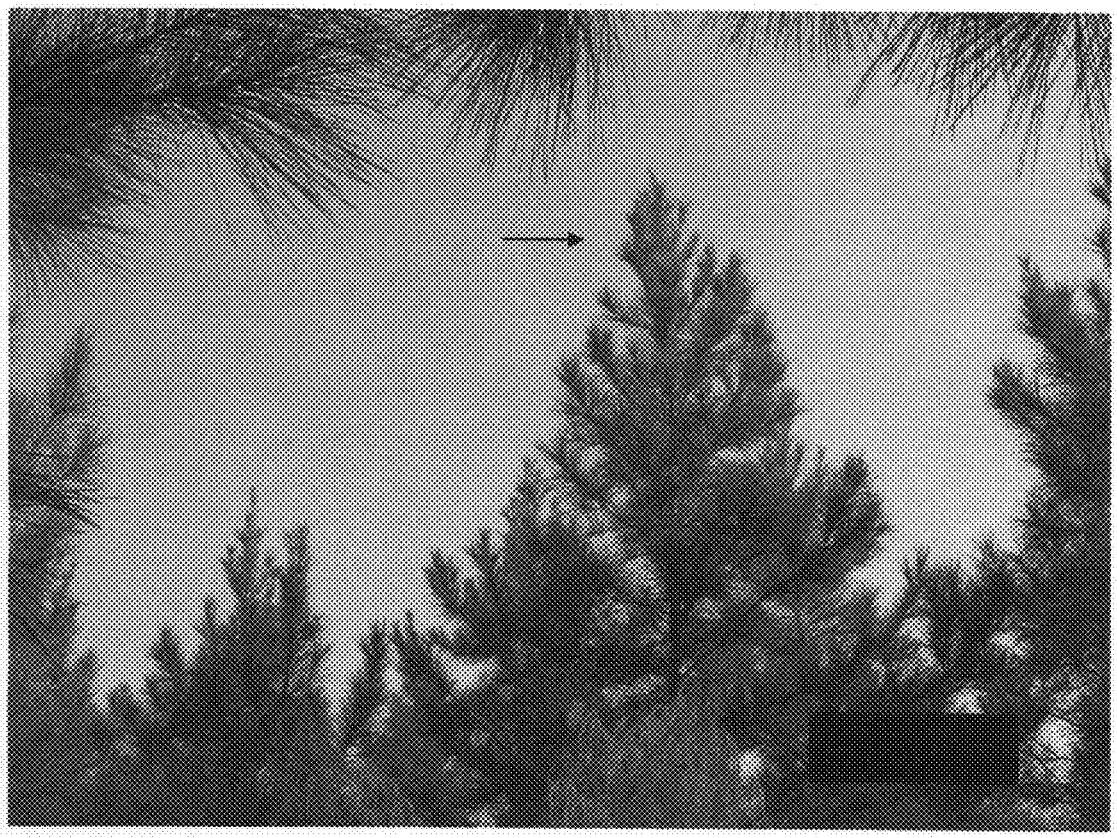
FIG. 1 is a photograph showing 'CF LP1-7696' ramet # 3 planted in Beulah, Tex. The picture was taken after five field growing seasons. The picture shows superiority of growth and medium crown width.
Figure 2:
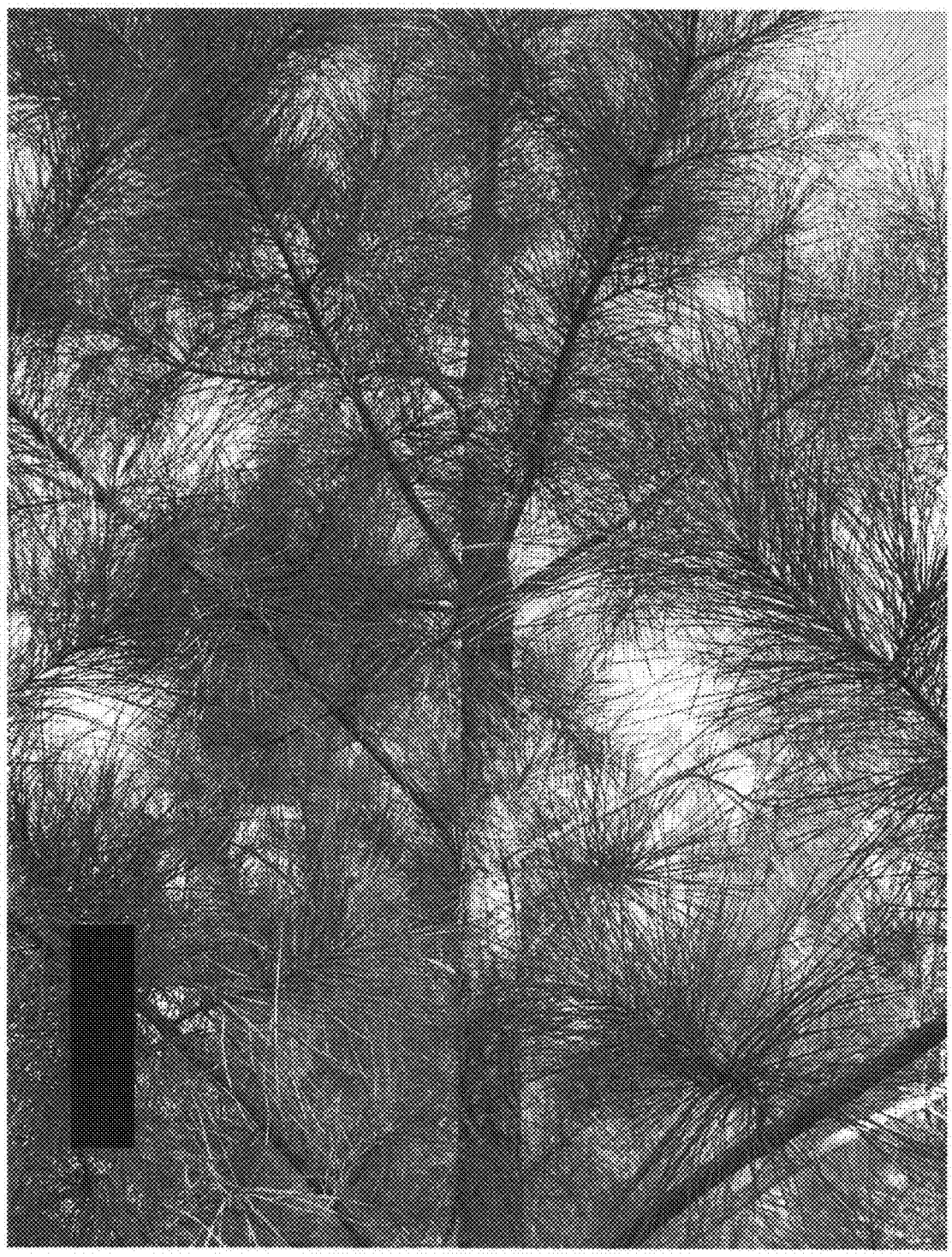
FIG. 2 is a photograph showing 'CF LP1-7696' ramet # 5 planted in Beulah, Tex. The picture was taken after five field growing seasons. The picture shows excellent stem straightness, medium number of whorls per unit stem length, medium angle between the stem and the branches, and medium branch diameter (relative to the size of the stem).

The botanical details of this new and distinct variety of loblolly pine tree follow. All color descriptions are made in reference to The Royal Horticultural Society (R.H.S.) Colour Chart (2005).

Parentage:

*Female parent.*—(Unknown) progeny of two first generation selections made in Cherokee County, Tex. and Tyler County, Tex.

*Male parent.*—(Unknown) progeny of an open pollinated first generation selection made in Montgomery County, Tex.

Leaf: Evergreen needles, 6 to 9 inches long, with (usually) three yellow-green needles per fascicle. The color of the foliage was taken from field established trees aged 6 years, but was not found to vary significantly with age. The color of the foliage was RHS 137A (60%) and 136A (40%).

Flower: Monoecious; males long cylindrical, red to yellow, in clusters at branch tips; females yellow to purple.

Fruit: Ovoid to cylindrical, 3 to 6 inch red-brown cones; umbo is armed with a short spine, maturing in early fall. Cones are sporadic in 5-7 year old plants.

Branch: Orange-brown in color, fine to moderately stout; buds are narrowly ovoid, light reddish brown.

Bark: Initially red- to gray-brown and scaly; older trees are ridged and furrowed, with somewhat rounded scaly plates; very old trees have red-brown, flat scaly plates.

Shape: A medium to large tree can reach well over 100 feet tall, self-prunes well and develops a fairly straight trunk and an oval, somewhat open crown.

Compared to unimproved loblolly pine trees, 'CF LP1-7696' is characterized by high growth rate, good resistance to fusiform rust (caused by *Cronartium quercuum* (Berk.) Miyabe ex Shirai f. sp. *fusiforme* (Cumm.) Burds. et Snow), excellent stem straightness, medium crown width, medium number of whorls, medium branch angle and medium branch diameter.

Average height: 20 ft after 5 field growing seasons

Maximum height: 24 ft after 5 field growing seasons

Average trunk diameter at breast height (4.5 feet above the soil level): 3.8 inches after 5 field growing seasons and 4.7 inches to 6.0 inches after 6 field growing seasons.

Sampling of Branch Characteristics: In order to sample branches from a consistent position from one tree to the next the following methodology was utilized. From a point nine feet from the base of the tree, the first complete whorl of limbs below was labeled "Whorl One" and the first complete whorl of limbs above labeled "Whorl Two". This sampling point was chosen because it is the midpoint of the basal sixteen foot log of each tree. A complete whorl was defined as one with at least three branches. All measurements were taken commencing on the South side of the tree and progressing anticlockwise around the stem. When more than three branches were available for measurement on the whorl the largest three branches, by basal diameter, were used for sampling. The following branch characteristics were measured after six field growing seasons.

Branch diameter: Diameter of each measured branch was taken at its base. Using a caliper the diameter of the branch, over bark, was measured to the closest $16^{th}$ of an inch. 'CF LP1-7696' has an average branch diameter of 0.63 inches at the base of the branch. Zygotic seedlings of the same genetic origin have an average branch diameter of 0.98 inches at the base of the branch.

Branch angle: Utilizing a large protractor, the angle of each branch was measured as its deviation from horizontal. Branch angles were recorded for the portion of the branch emerging from the stem of the tree with data rounded to the closest 10 degrees. 'CF LP1-7696' has an average branch angle of 29.50 degrees from horizontal. Zygotic seedlings of the same genetic origin have an average branch angle of 29.44 degrees from horizontal.

Branch length: The length of each sampled branch was measured directly with a graduated measurement pole. Branch lengths were recorded to the closest 0.5 feet. 'CF LP1-7696' has an average branch length of 6.48 feet. Zygotic seedlings of the same genetic origin have an average branch length of 8.8 feet.

Crown diameter: The width of the crown, at the point where branch measurements were taken, was directly measured with the use of a graduated measurement pole. A radial measurement was taken on the East and West side of each tree. Crown radius was measured to the closest 0.5 feet. Crown width data is presented as diameter of the crown. 'CF LP1-7696' has an average crown diameter of 8.65 feet. Zygotic seedlings of the same genetic origin have an average crown diameter of 11.37 feet.

Internode length: In proximity to the area of the stem utilized for branch measurements the mean internode length was determined for each tree. Internode distances for the calculation of the mean were directly measured from the stem of the tree using a graduated measurement pole. 'CF LP1-7696' has an average internode length of 1.22 feet. Zygotic seedlings of the same genetic origin have an average internode length of 1.25 feet.

Maximum trunk diameter at breast height (4.5 feet above the soil level): 4.4 inches after 5 field growing seasons Percent stem fusiform rust infection at age 5:0

Percent branch fusiform rust infection at age 5:5

Percent branch and stem fusiform rust infection at age 5:0

Percent dead ramets due to fusiform rust infection at age 5:0

Percent stem fusiform rust infection in the USDA Resistance Screening Center (Asheville, N.C.) tests after artificial inoculation with rust spores: 31% (compared to 76% infection in unimproved seedlings)

Propagation: propagated by somatic embryogenesis

Seeds: none produced at age 5 years of age, plants are not yet mature. Expected seed production by 12-15 years of age.

Use: high yield industrial plantations

Although the new variety of loblolly pine tree possesses the detailed characteristics noted above as a result of the growing conditions prevailing in the test locations, it is to be understood that the variations of the usual magnitude and characteristics incident to changes in growing conditions, irrigation, fertilization, pruning, pest control, climatic variations and the like are to be expected. An example of 'CF LP1-7696' can be found at The Campbell Group Beulah year 2003 line trial, Angelina county, Tex.

COMPARISON WITH PARENTS BY MICROSATELLITE ANALYSIS

Microsatellite markers (SSR's) were used to generate a unique DNA fingerprint for the variety. Young foliage samples from 6 ramets of LP1-7696 variety and from the parental trees used to make the LP1 cross were collected for DNA fingerprinting. The DNA extraction protocol of Doyle and Doyle (1987) was used after slight modifications. DNA fingerprinting of parents and the LP1-7696 variety was conducted using a set of nine microsatellite markers (Elsik et al., 2000; Auckland et al., 2002; Echt et al., 2008). Table 1 shows the sequences and conditions for each primer.

TABLE 1

ID's, sequences and conditions of SSR primers used in loblolly pine LP1-7696 variety.

| Primer full ID | UniSTS # | GenBank accession | SEQUENCE (5'-3') (SEQ ID NO:) |
|---|---|---|---|
| PtTX3011 | 508455 | BV728852 | F: AATTTGGGTGTATTTTTCT TAGA (SEQ ID NO: 1) R: AAAAGTTGAAGGAGTTG GTGATC (SEQ ID NO: 2) |
| PtTX3025 | 508459 | BV728855 | F: CACGCTGTATAATAACAA TCTA (SEQ ID NO: 3) R: GGATAACAATTTCACACA GGTTCTATATTCGCTTTTAG TTTC (SEQ ID NO: 4) |
| PtTX3034 | 508463 | BV728857 | F: CACGACGTTGTAAAACGA CTCAAAATGCAAAAGACG (SEQ ID NO: 5) R: ATTAGGACTGGGGATGA T (SEQ ID NO: 6) |
| PtTX3049 | 508467 | BV728826 | F: GAAGTGATAATGGCATA GCAAAAT (SEQ ID NO: 7) R: GCAGACCCGTGAAAGTA ATAAACAT (SEQ ID NO: 8) |
| PtTX3105 | 508475 | BV728847 | F: TGTCGGTGGAGTTGGCAG TAGACT (SEQ ID NO: 9) R: GCCCAGCGTTTCCTG (SEQ ID NO: 10) |
| PtTX3116 | 508479 | BV728848 | F: CACGACGTTGTAAAACGA CCTCCCAAAGCCTAAAGAA T (SEQ ID NO: 11) R: CATACAAGGCCTTATCTT ACAGAA (SEQ ID NO: 12) |
| PtTX3127 | 508483 | BV728849 | F: ACCCTTACTTTCAGAAGA GGATA (SEQ ID NO: 13) R: GGATAACAATTTCACACA GGAATTGGGGTTCAACTATT CTATTA (SEQ ID NO: 14) |
| PtSIFG_0566 | 516281 | BV728755 | F: CACGACGTTGTAAAACGA CACTTAGTGGGAAAGGGGG AA (SEQ ID NO: 15) R: GTTTCTTTTCCTCAGCCA AAAGCTCTC (SEQ ID NO: 16) |
| PtSIFG_4233 | 516353 | BV728685 | F: CACGACGTTGTAAAACGA CAGGGAAACCGCGGATTAT AG (SEQ ID NO: 17) R: GTTTCTTCCGGAATGAAG ATTGCAGTT (SEQ ID NO: 18) |

| Primer full ID | LABEL TAIL (F/R); E (end labeled) | $MgCl_2$ (mM) | Ta (° C) |
|---|---|---|---|
| PtTX3011 | E | 2.5 | 55 |
| PtTX3025 | R | 2.5 | 61 |
| PtTX3034 | F | 2.5 | 55 |
| PtTX3049 | E | 2.5 | 59 → 49 |
| PtTX3105 | E | 2.5 | 59 → 49 |
| PtTX3116 | F | 2.5 | 55 → 45 |
| PtTX3127 | R | 2.5 | 61 |
| PtSIFG_0566 | F | 2.5 | 65 → 55 |
| PtSIFG_4233 | F | 2.5 | 65 → 55 |

Ta = primer annealing temperature.

Microsatellite products were detected by M13 tailed primer (Oettling et al., 1995) or infrared dye(IRD)-labeled primer. The amplification products were electrophoresed on 5.5% Long Ranger polyacrylamide gels using a LiCor 4200 automated sequencer (LiCor Inc., Lincoln, Neb.).

The observed parental genotypes and their expected offspring's genotypes at nine studied SSR loci are presented in Table 2. LP1-7696 fingerprint based on nine loci is presented in Table 3.

TABLE 2

Parental genotypes and their expected offspring's genotypes at nine SSR loci.

| Primer | Genotype Female | Genotype Male | Expected offspring genotypes | | | |
|---|---|---|---|---|---|---|
| PtTX3011 | 157/193 | 157/193 | 157/157 | 157/193 | 193/193 | |
| PtTX3025 | 277/289 | 274/277 | 277/274 | 227/227 | 289/274 | 289/277 |
| PtTX3127 | 207/210 | 204/207 | 207/204 | 207/207 | 210/204 | 210/207 |
| PtTX3034 | 228/228 | 216/220 | 228/216 | 228/220 | | |
| PtTX3049 | 311/313 | 323/325 | 311/323 | 311/325 | 313/323 | 313/325 |
| PtTX3116 | 147/150 | 159/180 | 147/159 | 147/180 | 150/159 | 150/180 |
| PtTX3105 | 169/190 | 169/184 | 169/169 | 169/184 | 190/169 | 190/184 |
| SIFG0566 | 133/139 | 145/145 | 133/145 | 139/145 | | |
| SIFG4233 | 127/127 | 129/137 | 127/129 | 127/137 | | |

TABLE 3

LP1-7696 genotypes at nine SSR loci. Allelic sizes include LiCor primer tails for M13 tailed primers.

| PtTX3011 | | PtTX3025 | | PtTX3127 | |
|---|---|---|---|---|---|
| Allele1 | Allele2 | Allele1 | Allele2 | Allele1 | Allele2 |
| 157 | 193 | 274 | 289 | 204 | 207 |
| **PtTX3034** | | **PtTX3049** | | **PtTX3116** | |
| Allele1 | Allele2 | Allele1 | Allele2 | Allele1 | Allele2 |
| 216 | 228 | 311 | 325 | 150 | 180 |
| **PtTX3105** | | **SIFG0566** | | **SIFG4233** | |
| Allele1 | Allele2 | Allele1 | Allele2 | Allele1 | Allele2 |
| 169 | 190 | 139 | 145 | 127 | 137 |

References:

Auckland, L., T. Bui, Y. Zhou, M. Shepherd and C. Williams. 2002. Conifer Microsatellite Handbook Corporate Press, Raleigh, N.C., USA.

Doyle, J.J. and J.L. Doyle. 1987. A rapid DNA isolation procedure for small quantities of fresh tissue. Phytochemical bulletin 19:11-15.

Echt, C.S., Saha, S. and Nelson, C.D. 2008. Southern Institute of Forest Genetics, USDA Forest Service Southern Research Station, 23332 Mississippi 67, Saucier, MS 39574, USA. On-line genetic database: http://www.ncbi.nlm.nih.gov/unists Elsik, C.G., Minihan, V.T., Hall, S.E., Scarpa, A.M. and Williams, C.G. 2000. Low-copy microsatellite markers for *Pinus taeda* L. Genome 43(3):550-555.

Oetting, W.S., H.K. Lee, D.J. Flanders, G.L. Wiesner, T.A. Sellers and R.A. King. 1995. Linkage analysis with multiplexed short tandem repeat polymorphisms using infrared florescence and M13 tailed primers. Genomics 30:450-458.

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1 aatttgggtg tatttttctt aga 23

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2 aaaagttgaa ggagttggtg atc 23

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3 cacgctgtat aataacaatc ta 22

<210> SEQ ID NO 4
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 4 ggataacaat ttcacacagg ttctatattc gcttttagtt tc 42

<210> SEQ ID NO 5
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 5 cacgacgttg taaaacgact caaaatgcaa aagacg 36

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 6 attaggactg gggatgat 18

<210> SEQ ID NO 7

-continued

<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 7 gaagtgataa tggcatagca aaat 24

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 8 gcagacccgt gaaagtaata aacat 25

<210> SEQ ID NO 9
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 9 tgtcggtgga gttggcagta gact 24

<210> SEQ ID NO 10
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 10 gcccagcgtt tcctg 15

<210> SEQ ID NO 11
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 11 cacgacgttg taaaacgacc tcccaaagcc taaagaat 38

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 12 catacaaggc cttatcttac agaa 24

<210> SEQ ID NO 13
<211> LENGTH: 23
<212> TYPE: DNA
<213> ORGANISM: Artificial Sequence
<220> FEATURE:
<223> OTHER INFORMATION: Synthetic Oligonucleotide -continued

<400> SEQUENCE: 13 acccttactt tcagaagagg ata 23

<210> SEQ ID NO 14
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 14 ggataacaat ttcacacagg aattggggtt caactattct atta 44

<210> SEQ ID NO 15
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 15 cacgacgttg taaaacgaca cttagtggga aagggggaa 39

<210> SEQ ID NO 16
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 16 gtttcttttc ctcagccaaa agctctc 27

<210> SEQ ID NO 17
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 17 cacgacgttg taaaacgaca gggaaaccgc ggattatag 39

<210> SEQ ID NO 18
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 18 gtttcttccg gaatgaagat tgcagtt 27

We claim:

1. A new and distinct variety of loblolly pine tree named ‘CF LP1-7696’ substantially as described and illustrated.

* * * * *